United States Patent [19]

Staibano

[11] Patent Number: 4,705,651
[45] Date of Patent: Nov. 10, 1987

[54] PROCESS FOR THE PREPARATION OF DIPHOSPHONIC ACIDS

[75] Inventor: Giorgio Staibano, Coltano, Italy

[73] Assignee: Istituto Gentili S.p.A., Pisa, Italy

[21] Appl. No.: 786,815

[22] Filed: Oct. 11, 1985

[30] Foreign Application Priority Data

Oct. 29, 1984 [IT] Italy ............................. 23362 A/84

[51] Int. Cl.⁴ .............................................. C07F 9/38
[52] U.S. Cl. ....................... 260/502.5 C; 260/502.4 A
[58] Field of Search .................. 260/502.4 A, 502.5 C

[56] References Cited

U.S. PATENT DOCUMENTS

| | | | |
|---|---|---|---|
| 3,366,677 | 1/1968 | Quimby | 260/502.4 A |
| 4,054,598 | 10/1977 | Blum et al. | 260/502.5 C |
| 4,060,546 | 11/1977 | Blaser et al. | 260/502.4 A |
| 4,267,108 | 5/1981 | Blum et al. | 260/502.5 C |
| 4,304,734 | 12/1981 | Jary et al. | 260/502.5 C |

FOREIGN PATENT DOCUMENTS

| | | | |
|---|---|---|---|
| 2846835 | 5/1980 | Fed. Rep. of Germany | 260/502.5 C |
| 783300 | 12/1980 | U.S.S.R. | 260/502.4 A |

*Primary Examiner*—J. E. Evans
*Attorney, Agent, or Firm*—Bucknam and Archer

[57] ABSTRACT

The invention concerns a process for the preparation of diphosphonic acids starting from carboxylic acids, a phosphorus trihalide and orthophosphorous acid, without solvents, using particular molar ratios and conditions so as to keep the reaction mixture fluid and carrying out the hydrolysis only with boiling water.

1 Claim, No Drawings

PROCESS FOR THE PREPARATION OF DIPHOSPHONIC ACIDS

The present invention refers to a process for the preparation of diphosphonic acids, particularly of 4-amino-1-hydroxybutylidene-1,1-diphosphonic acid (ABDP) and 6-amino-1-hydroxyhexylidene-1,1-diphosphonic acid (AHDP), compounds useful in human therapy in the treatment of ostheopathies.

Different processes for the preparation of diphosphonic acids are known; for instance, German Offenlegungsschrift No. 2,130,794 discloses the preparation of 3-amino-1-hydroxypropylidene-1,1-diphosphonic acid by reacting orthophosphorous acid, a phosphorus trihalide and a carboxylic acid; said method has been applied to other diphosphonic acids having an aliphatic chain of different length (Kabacnick M.I. et al.-Izv. Akad. Nauk SSSR, chemical series 2, 433-1978) and it has been further developed by Czechoslovak researchers.

Ger. Offen. No. 3,016,289 discloses the preparation of 6-amino-1-hydroxyhexylidene-1,1-diphosphonic and 4-amino-1-hydroxybutylidene-1,1-diphosphonic acids, pointing out the opportunity of carrying out a drastic hydrolysis of the reaction products with strong, non-oxydizing acids, in order to obtain a more pure product.

All the known processes require the presence of solvents, particularly of chlorobenzene, which must be then removed during the work-up procedures. The reported yields in the different processes range from 45% to 55%.

The process according to the present invention is characterized in that carboxylic acids, orthophosphorous acid and a phosphorus trihalide are reacted in the absence of solvents and in such ratios as to keep the reaction bulk in a fluid, and therefore shakable condition, and that the hydrolysis is carried out by means of water alone, without recovery of the intermediate product. The diphosphonic acid is then recovered by adding a $C_1$–$C_3$ lower alcohol.

The hydrolysis is carried out at the boiling temperature for a period ranging from 4 to 12 hours, preferably for about 6 hours. As a phosphorus trihalide, phosphorus trichloride is preferably used. The yields range from 60 to 70% and the obtained product is particularly pure.

The advantages deriving from this process are multiple: in addition to higher reaction yield, the complete absence of solvents, mainly of the halogenated ones, is particularly desirable for the intended pharmaceutical use of some of the diphosphonic acids which can be obtained by the process of the invention, particularly ABDP and AHDP. It is in fact known that even residual traces of halogenated solvents may have a negative influence on the safety of use of pharmaceutical active principles. The absence of solvents makes also possible to process large amounts in reduced volumes, allowing a higher productivity, at the industrial level, with the same reaction volumes available, with consequent decrease of the production costs, the latter being further improved also by the elimination of two steps of the procedure: the solvent removal and the recovery of the product to be hydrolyzed.

The preferred molar ratios between the reagents are about 1:1.25:2 for the carboxylic acid, phosphorous acid and phosphorus trihalide, respectively.

The following non-limitative examples further illustrate the process according to the invention.

EXAMPLE 1

4-Amino-1-hydroxybutylidene-1,1-diphosphonic acid (ABDP)

Orthophosphorous acid (102.7 g; 1.25 moles) is introduced into a 2 liter-flask with condenser, stirrer and dropping funnel, placed on a thermostatized bath; the air is then removed with a nitrogen stream which is continued during all the reaction. The acid is melted, by heating the bath to 95° C. When melting is complete, 4-aminobutyrric acid (103.3 g; 1 mole) is added under stirring which is continued till obtaining a doughy fluid.

Phosphorus trihalide (176 ml; 2 moles) is added dropwise, by means of the dropping funnel, causing the mixture to boil and the evolution of gaseous hydrochloric acid which is damped by means of a suitable trap. The addition rate is adjusted so as to keep a constant reflux: it takes about 60 minutes. When the addition is nearly over, the mixture swells, slowly hardening. Stirring is continued as long as possible, whereafter the mixture is heated for further 3 hours.

Without cooling, but removing the bath, water (300 ml) is added, first slowly and then quickly. Heating and stirring are started again. Decolorizing charcoal is added and the mixture is boiled for about 5 minutes, then hot-filtered on paper and the filtrate is refluxed for 6 hours.

After cooling, the solution is slowly poured in stirred methanol (1500 ml) causing thereby the separation of a white solid which is collected and dried (161 g; 64.6%). The diphosphonic acid so obtained is in form of white, fine powder, having the following characteristics.

| Elemental analysis: for $C_4H_{13}NO_7P_2$ (249.12) | | | |
| --- | --- | --- | --- |
| | C | H | N | P |
| Calc. % | 19.28 | 5.26 | 5.64 | 24.86 |
| Found % | 19.41 | 5.40 | 5.50 | 24.53. |

Determination of the moisture content

The sample, tested according to Karl-Fischer, has a not significant moisture content.

Potentiometric titration

The potentiometric titration curve is obtained by adding 0.1 N NaOH to a solution of 188 mg of sample dissolved in 75 ml of water. The profile of said curve is characterized by two marked flex-points at pH 4.4 and 9.0, corresponding to an addition of titrating agent of 7.5 and 15.2 ml, respectively.

From the reported values, an equivalent weight of 250 for the first neutral point and of 248 for the second one (mean equivalent weight: 249) are calculated. The molecular weight of ABDP is 249.12.

Complexometric titration

The complexometric titration carried out with thorium nitrate on 38.68 mg of the compound, shows a neat colour change point at an addition of 5.4 ml of titrating agent. From said value, it is possible to compute, for the tested compound, an equivalent weight of 125, in agreement with the presence of two phosphonic groups per molecule.

Infrared absorption

The IR spectrum recorded on KBr pellet, shows characteristics band at:

| | |
|---|---|
| 3600–2500 cm$^{-1}$ | complex band due to the overlapping of the stretchings of the acid and alcohol OH groups, of NH$_3^\oplus$ groups and aliphatic CH. |
| 1650, 1605, 1500 | bands due to the bending of the NH$_2$ groups partially salified by phosphonic groups. |
| 1160 | stretching of the P=O bond |
| 1040 | stretching of the C—O bond |
| 960, 930 | stretching of the P—O bond |
| 600–400 | stretching of the skeleton bonds involving mainly the part of the molecule containing phosphorus atoms. |

Proton nuclear magnetic resonance ($^1$H-NMR)

The $^1$H-NMR spectrum recorded in D$_2$O/D$_2$SO$_4$ shows two broad signals at $\delta$2.6 ppm (CH$_2$-$\beta$ and CH$_2$-$\gamma$ with respect to the NH$_2$ group) and 3.5 ppm (CH$_2$-$\alpha$ to the NH$_2$ group) having a relative intensity of 2:1.

Carbon nuclear magnetic resonance ($^{13}$C-NMR)

The $^{13}$C-NMR spectrum recorded in D$_2$O/D$_2$SO$_4$ shows signals at $\delta$20 ppm (CH$_2$-13 to the NH$_2$ group), 28 ppm (CH$_2$-$\delta$ to the NH$_2$ group), 39 ppm (CH$_2$-$\alpha$ to the NH$_2$ group) and a triplet centered at 72 ppm (C-$\delta$ to the NH$_2$ group, J$_{C-P}$ 156 Hz).

Phosphorus nuclear magnetic resonance ($^{31}$P-NMR)

The $^{31}$P-NMR spectrum recorded in D$_2$O/D$_2$SO$_4$ shows a single signal at 9 ppm, showing that the two phosphorus atoms are chemically and magnetically equivalent.

EXAMPLE 2

6-Amino-1-hydrohyhexylidene-1,1-diphosphonic acid (AHDP)

The same procedure of the previous example is used, with the same molecular ratios.

The characteristics of the product, obtained in a 71% yield, are the following:

| Elemental analysis: for C$_6$H$_{17}$NO$_7$P$_2$ (277.14) | | | | |
|---|---|---|---|---|
| | C | H | N | P |
| Calc. % | 25.99 | 6.48 | 5.05 | 22.35 |
| Found % | 26.07 | 6.26 | 5.07 | 22.75. |

Determination of the moisture content

The tested compound does not show appreciable weight loss after drying at 100° C./0.1 mmHg.

Potentiometric titration

The potentiometric titration curve obtained by adding 0.1N NaOH to a solution of 200 mg of sample suspended in 75 ml of water, is characterized by two marked flex-points at pH 4.75 and 9.05, corresponding to an addition of titrating agent of 7.1 and 14.4 ml, respectively. From the reported values, an equivalent weight of 282 for the first neutral point and of 274 for the second one and a mean equivalent weight of 278 are calculated. (AHDP molecular weight=277.153).

Complexometric titration

The complexometric titration carried out with thorium nitrate on 124.7 mg of the compound shows a neat colour change point at an addition of 15.8 ml of titrating agent. From said value, it is possible to compute, for the tested compound, an equivalent weight of 137, in agreement with the presence of two phosphonic groups per molecule.

Infrared absorption

The IR spectrum recorded on KBr pellet, shows characteristics band at:

| | |
|---|---|
| 3600–2000 cm$^{-1}$ | complex band due to the overlapping of the stretchings of the acid and alcohol OH groups, of NH$_3^\oplus$ groups and aliphatic CH. |
| 1640, 1580, 1495 | bands due to the bending of the NH$_2$ groups partially salified by phosphonic groups |
| 1200–900 | stretching of the P=O bond, C—O and P—O groups |
| 600–400 | skeleton bonds involving mainly the part of the molecule containing phosphorus atoms. |

Proton nuclear magnetic resonance ($^1$H-NMR)

The $^1$H-NMR spectrum recorded in D$_2$O/D$_2$SO$_4$ (1:1 vol/vol), shows a broad signal at 1.6–3.0 ppm of relative intensity 4 (CH$_2$-$\gamma$, $\delta$, $\beta$, and $\epsilon$ to the NH$_2$ group) and a broad triplet at 3.5 ppm (CH$_2$-$\alpha$ to the NH$_2$ group) having a relative intensity of 1.

Carbon nuclear magnetic resonance ($^{13}$C-NMR)

The $^{13}$C-NMR spectrum recorded in D$_2$O/D$_2$SO$_4$ shows signals at $\delta$27 ppm (CH$_2$-$\gamma$ to the NH$_2$ group), 30 ppm (CH$_2$-$\delta$ to the NH$_2$ group), 31 ppm (CH$_2$-$\beta$ to the NH$_2$ group), 35 (CH$_2$-$\epsilon$ to the NH$_2$ group), 41 (CH$_2$-$\alpha$ to the NH$_2$ group) and a triplet centered at 67 ppm (C-$\zeta$ to the NH$_2$ group, J$_{C-P}$ 160 Hz).

Phosphorus nuclear magnetic resonance ($^{31}$P-NMR)

The $^{31}$P-NMR spectrum recorded in D$_2$O/D$_2$SO$_4$ shows a single signal at 9.5 ppm, showing that the two phosphorus atoms are chemically and magnetically equivalents.

I claim:

1. In the process of preparation of a compound I which is 4-amino-1-hydroxybutane-1,1-diphosphonic acid or 6-amino-1-hydroxyhexane-1,1-diphosphonic acid wherein a compound II which is 4-aminobutyric acid or 6-aminocaproic acid respectively is reacted with compound III which is orthophosphorous acid and with compound IV which is phosphorus trichloride and the product is hydrolyzed, the improvement which consists of melting orthophosphorous acid, adding said compound II in the ratio of 1:1.25 mole of compound II to compound III, in the absence of a solvent; then adding 2 moles of phosphorous trichloride, maintaining the mixture under reflux until the mixture hardens, heating three hours, then adding water, refluxing 4–12 hours to obtain a reaction mixture, pouring said reaction mixture into an alcohol of 1–3 carbon atoms and isolating said product I from the reaction mixture.

* * * * *